(12) United States Patent
Verard et al.

(10) Patent No.: US 11,426,254 B2
(45) Date of Patent: Aug. 30, 2022

(54) METHOD AND APPARATUS FOR VIRTUAL ENDOSCOPY

(71) Applicant: Medtronic Navigation, Inc., Louisville, CO (US)

(72) Inventors: Laurent Verard, Katonah, KY (US); Paul Kessman, Lakewood, CO (US); Mark W. Hunter, Broomfield, CO (US)

(73) Assignee: Medtronic Navigation, Inc., Louisville, CO (US)

(*) Notice: Subject to any disclaimer, the term of this patent is extended or adjusted under 35 U.S.C. 154(b) by 178 days.

(21) Appl. No.: 16/725,386

(22) Filed: Dec. 23, 2019

(65) Prior Publication Data

US 2020/0129262 A1    Apr. 30, 2020

Related U.S. Application Data

(60) Division of application No. 15/817,914, filed on Nov. 20, 2017, now Pat. No. 10,512,522, which is a
(Continued)

(51) Int. Cl.
*A61B 90/00*    (2016.01)
*A61B 34/20*    (2016.01)
(Continued)

(52) U.S. Cl.
CPC .............. *A61B 90/36* (2016.02); *A61B 34/20* (2016.02); *A61B 34/10* (2016.02); *A61B 90/361* (2016.02);
(Continued)

(58) Field of Classification Search
CPC ......... A61B 90/36; A61B 34/20; A61B 34/10; A61B 90/361; A61B 2017/00703;
(Continued)

(56) References Cited

U.S. PATENT DOCUMENTS

| 4,821,731 A | * | 4/1989 | Martinelli | A61B 34/20 600/463 |
| 5,345,938 A | * | 9/1994 | Nishiki | G16H 15/00 600/463 |

(Continued)

FOREIGN PATENT DOCUMENTS

| WO | 9729682 | 8/1997 |
| WO | 9836684 | 8/1998 |

(Continued)

OTHER PUBLICATIONS

U.S. Appl. No. 10/223,847, U.S. Pat. No. 6,892,090, filed Aug. 19, 2002, Verard, et al.

(Continued)

*Primary Examiner* — Bo Joseph Peng
(74) *Attorney, Agent, or Firm* — Harness, Dickey & Pierce, P.L.C.

(57) ABSTRACT

A surgical instrument navigation system is provided that visually simulates a virtual volumetric scene of a body cavity of a patient from a point of view of a surgical instrument residing in the cavity of the patient. The surgical instrument navigation system includes: a surgical instrument; an imaging device which is operable to capture scan data representative of an internal region of interest within a given patient; a tracking subsystem that employs electromagnetic sensing to capture in real-time position data indicative of the position of the surgical instrument; a data processor which is operable to render a volumetric perspective image of the internal region of interest from a point of view of the surgical instrument; and a display which is operable to display the volumetric perspective image of the patient.

14 Claims, 3 Drawing Sheets

Related U.S. Application Data continuation of application No. 11/068,342, filed on Feb. 28, 2005, now abandoned, which is a continuation of application No. 10/223,847, filed on Aug. 19, 2002, now Pat. No. 6,892,090.

(51) Int. Cl.
  *A61B 17/00* (2006.01)
  *A61B 34/10* (2016.01)
  *A61B 34/00* (2016.01)

(52) U.S. Cl.
  CPC .............. *A61B 2017/00703* (2013.01); *A61B 2034/101* (2016.02); *A61B 2034/105* (2016.02); *A61B 2034/107* (2016.02); *A61B 2034/2051* (2016.02); *A61B 2034/2055* (2016.02); *A61B 2034/2072* (2016.02); *A61B 2034/256* (2016.02); *A61B 2090/365* (2016.02); *A61B 2090/367* (2016.02)

(58) Field of Classification Search
  CPC ........ A61B 2034/101; A61B 2034/105; A61B 2034/107; A61B 2034/2051; A61B 2034/2055; A61B 2034/2072; A61B 2034/256; A61B 2090/365; A61B 2090/367
  See application file for complete search history.

(56) References Cited

U.S. PATENT DOCUMENTS

| | | | |
|---|---|---|---|
| 5,617,857 A | | 4/1997 | Chader et al. |
| 5,622,170 A | | 4/1997 | Schulz |
| 5,807,235 A | | 9/1998 | Heff |
| 5,830,145 A | * | 11/1998 | Tenhoff ................ A61B 8/4461 600/463 |
| 5,885,218 A | * | 3/1999 | Teo .................... G01S 7/52034 600/443 |
| 5,979,453 A | * | 11/1999 | Savage .............. A61B 18/1477 128/898 |
| 6,038,468 A | * | 3/2000 | Rex ......................... A61B 5/06 600/424 |
| 6,175,757 B1 | * | 1/2001 | Watkins ................ A61B 5/055 128/916 |
| 6,436,073 B1 | * | 8/2002 | Von Teichert ........ A61M 5/158 128/DIG. 26 |
| 6,892,090 B2 | | 5/2005 | Verard et al. |
| 7,697,972 B2 | | 4/2010 | Verard et al. |
| 10,512,522 B2 | | 12/2019 | Verard et al. |
| 2001/0007919 A1 | * | 7/2001 | Shahidi .................. A61B 5/064 600/427 |
| 2002/0049375 A1 | | 4/2002 | Strommer et al. |
| 2002/0055674 A1 | | 5/2002 | Ben-Haim et al. |
| 2002/0065455 A1 | | 5/2002 | Ben-Haim et al. |
| 2002/0075994 A1 | | 6/2002 | Shahidi et al. |
| 2002/0077544 A1 | * | 6/2002 | Shahidi .................. A61B 90/36 600/424 |
| 2002/0077546 A1 | | 6/2002 | Aldefeld et al. |
| 2002/0106116 A1 | | 8/2002 | Knoplioch et al. |
| 2005/0143651 A1 | | 6/2005 | Verard et al. |

FOREIGN PATENT DOCUMENTS

| | | |
|---|---|---|
| WO | 0055812 | 9/2000 |
| WO | 0056215 | 9/2000 |
| WO | 0126050 | 4/2001 |

OTHER PUBLICATIONS

U.S. Appl. No. 11/068,342, 2005-0143651. filed Feb. 28, 2005, Verard, et al.
U.S. Appl. No. 15/817,914, U.S. Pat. No. 10,512,522, filed Nov. 20, 2017, Verard, et al.
European Office Action dated Jun. 1, 2011 claiming benefit of EP SN 0301803016, filed Aug. 12, 2003 which claims benefit of U.S. Appl. No. 10/223,847, filed Aug. 19, 2002.
European Search Report for EP 03 01 8301 dated Oct. 30, 2003.
Lorigo et al., Codimension-two geodesci active contours for the segmentation of tubular structures, Computer Vision and Pattern Recognition, 2000. Proceedings. IEEE Conference, pp. 444-451 vol. 1.
Partial European Search Report for EP 08 15 1389 dated Jun. 24, 2008.
Partial European Search Report for EP 08 15 1389 dated Mar. 20, 2008.

* cited by examiner

METHOD AND APPARATUS FOR VIRTUAL ENDOSCOPY

CROSS-REFERENCE TO RELATED APPLICATIONS

This application is a divisional of U.S. patent application Ser. No. 15/817,914 filed on Nov. 20, 2017; which is a continuation of U.S. patent application Ser. No. 11/068,342 filed on Feb. 28, 2005, now abandoned; which is a continuation of U.S. patent application Ser. No. 10/223,847 filed on Aug. 19, 2002, now U.S. Pat. No. 6,892,090 issued on May 10, 2005. The disclosures of the above applications are incorporated herein by reference.

FIELD

The present teachings relates generally to surgical instrument navigation systems and, more particularly, to a system that visually simulates a virtual volumetric scene of a body cavity from a point of view of a surgical instrument residing in a patient.

BACKGROUND

Precise imaging of portions of the anatomy is an increasingly important technique in the medical and surgical fields. In order to lessen the trauma to a patient caused by invasive surgery, techniques have been developed for performing surgical procedures within the body through small incisions with minimal invasion. These procedures generally require the surgeon to operate on portions of the anatomy that are not directly visible, or can be seen only with difficulty. Furthermore, some parts of the body contain extremely complex or small structures and it is necessary to enhance the visibility of these structures to enable the surgeon to perform more delicate procedures. In addition, planning such procedures required the evaluation of the location and orientation of these structures within the body in order to determine the optimal surgical trajectory.

Endoscopy is one commonly employed technique for visualizing internal regions of interest within a patient. Flexible endoscopes enable surgeons to visually inspect a region prior to or during surgery. However, flexible endoscopes are relatively expensive, limited in flexibility due to construction and obscured by blood and other biological materials.

Therefore, it is desirable to provide a cost effective alternative technique for visualizing an internal regions of interest within a patient.

SUMMARY

A surgical instrument navigation system is provided that visually simulates a virtual volumetric scene of a body cavity of a patient from a point of view of a surgical instrument residing in the patient. The surgical instrument navigation system generally includes: a surgical instrument, such as a guide wire or catheter; a tracking subsystem that captures real-time position data indicative of the position (location and/or orientation) of the surgical instrument; a data processor which is operable to render a volumetric image of the internal region of interest from a point of view of the surgical instrument; and a display which is operable to display the volumetric image of the patient. The surgical instrument navigation system may also include an imaging device which is operable to capture 2D and/or 3D volumetric scan data representative of an internal region of interest within a given patient.

For a more complete understanding of the present teachings, reference may be made to the following specification and to the accompanying drawings.

DETAILED DESCRIPTION OF VARIOUS EMBODIMENTS

Figure 1:
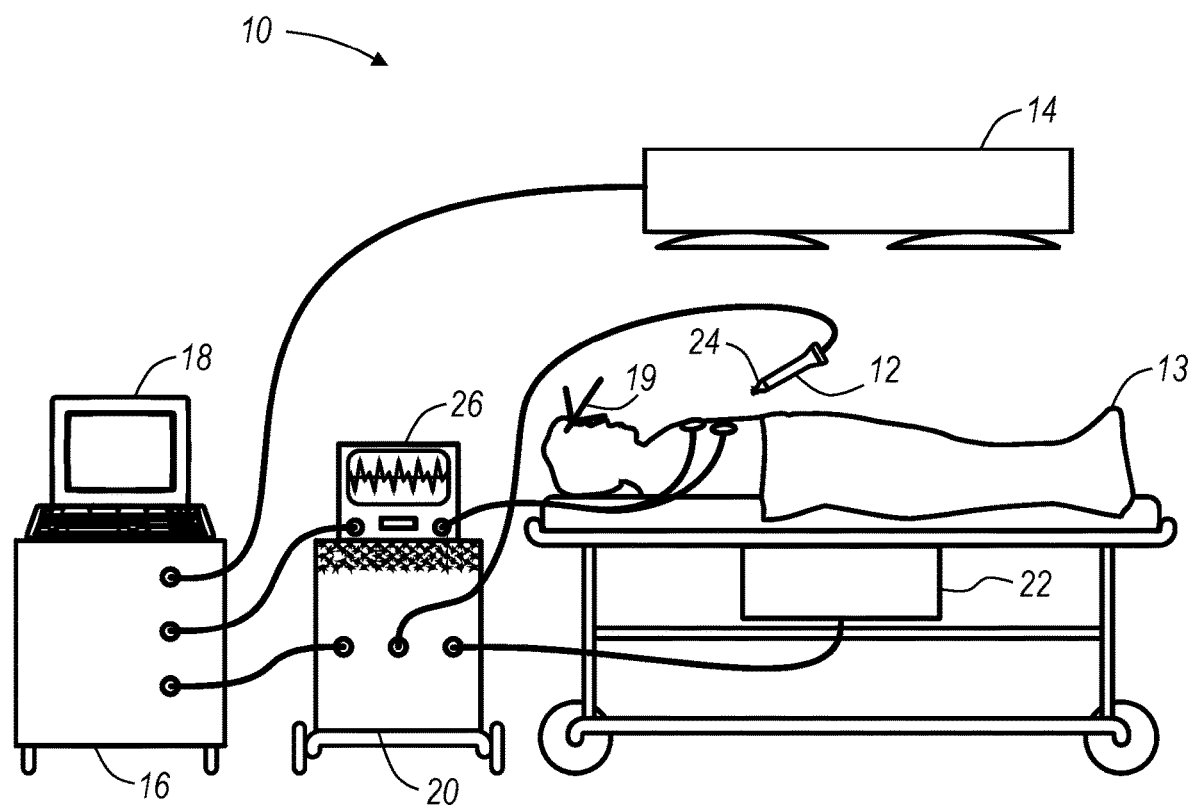
FIG. 1 is a diagram of an exemplary surgical instrument navigation system according to various embodiments.

FIG. 1 is a diagram of an exemplary surgical instrument navigation system 10. According to various embodiments, the surgical instrument navigation system 10 is operable to visually simulate a virtual volumetric scene within the body of a patient, such as an internal body cavity, from a point of view of a surgical instrument 12 residing in the cavity of a patient 13. To do so, the surgical instrument navigation system 10 is primarily comprised of a surgical instrument 12, a data processor 16 having a display 18, and a tracking subsystem 20. The surgical instrument navigation system 10 may further include (or accompanied by) an imaging device 14 that is operable to provide image data to the system.

The surgical instrument 12 is preferably a relatively inexpensive, flexible and/or steerable catheter that may be of a disposable type. The surgical instrument 12 is modified to include one or more tracking sensors that are detectable by the tracking subsystem 20. It is readily understood that other types of surgical instruments (e.g., a guide wire, a pointer probe, a stent, a seed, an implant, an endoscope, etc.) are also within the scope of the present teachings. It is also envisioned that at least some of these surgical instruments may be wireless or have wireless communications links. It is also envisioned that the surgical instruments may encompass medical devices which are used for exploratory purposes, testing purposes or other types of medical procedures.

Figure 2:
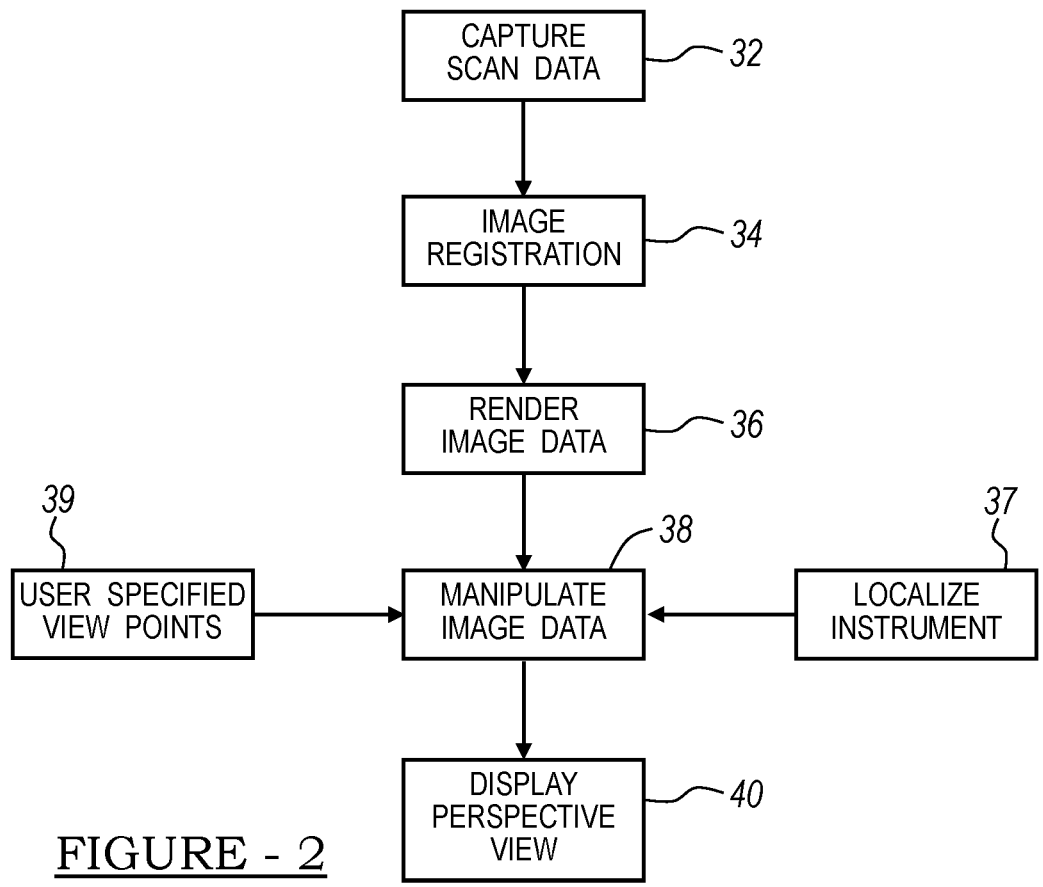
FIG. 2 is a flowchart that depicts a technique for simulating a virtual volumetric scene of a body cavity from a point of view of a surgical instrument positioned within the patient according to various embodiments.

Referring to FIG. 2, the imaging device 14 is used to capture volumetric scan data 32 representative of an internal region of interest within the patient 13. The three-dimensional scan data is preferably obtained prior to surgery on the patient 13. In this case, the captured volumetric scan data may be stored in a data store associated with the data processor 16 for subsequent processing. However, one skilled in the art will readily recognize that the principles of the present teachings may also extend to scan data acquired during surgery. It is readily understood that volumetric scan data may be acquired using various known medical imaging devices 14, including but not limited to a magnetic resonance imaging (MRI) device, a computed tomography (CT) imaging device, a positron emission tomography (PET)

imaging device, a 2D or 3D fluoroscopic imaging device, and 2D, 3D or 4D ultrasound imaging devices. In the case of a two-dimensional ultrasound imaging device or other two-dimensional image acquisition device, a series of two-dimensional data sets may be acquired and then assembled into volumetric data as is well known in the art using a two-dimensional to three-dimensional conversion.

A dynamic reference frame 19 is attached to the patient proximate to the region of interest within the patient 13. To the extent that the region of interest is a vessel or a cavity within the patient, it is readily understood that the dynamic reference frame 19 may be placed within the patient 13. To determine its location, the dynamic reference frame 19 is also modified to include tracking sensors detectable by the tracking subsystem 20. The tracking subsystem 20 is operable to determine position data for the dynamic reference frame 19 as further described below.

The volumetric scan data is then registered as shown at 34. Registration of the dynamic reference frame 19 generally relates information in the volumetric scan data to the region of interest associated with the patient. This process is referred to as registering image space to patient space. Often, the image space must also be registered to another image space. Registration is accomplished through knowledge of the coordinate vectors of at least three non-collinear points in the image space and the patient space.

Registration for image guided surgery can be completed by different known techniques. First, point-to-point registration is accomplished by identifying points in an image space and then touching the same points in patient space. These points are generally anatomical landmarks that are easily identifiable on the patient. Second, surface registration involves the user's generation of a surface in patient space by either selecting multiple points or scanning, and then accepting the best fit to that surface in image space by iteratively calculating with the data processor until a surface match is identified. Third, repeat fixation devices entail the user repeatedly removing and replacing a device (i.e., dynamic reference frame, etc.) in known relation to the patient or image fiducials of the patient. Fourth, automatic registration by first attaching the dynamic reference frame to the patient prior to acquiring image data. It is envisioned that other known registration procedures are also within the scope of the present teachings, such as that disclosed in U.S. Ser. No. 09/274,972, filed on Mar. 23, 1999, entitled "NAVIGATIONAL GUIDANCE VIA COMPUTER-ASSISTED FLUOROSCOPIC IMAGING", which is hereby incorporated by reference.

During surgery, the surgical instrument 12 is directed by the surgeon to the region of interest within the patient 13. The tracking subsystem 20 preferably employs electro-magnetic sensing to capture position data 37 indicative of the location and/or orientation of the surgical instrument 12 within the patient. The tracking subsystem 20 may be defined as a localizing device 22 and one or more electro-magnetic sensors 24 may be integrated into the items of interest, such as the surgical instrument 12. In one embodiment, the localizing device 22 is comprised of three or more field generators (transmitters) mounted at known locations on a plane surface and the electro-magnetic sensor (receivers) 24 is further defined as a single coil of wire. The positioning of the field generators (transmitter), and the sensors (receivers) may also be reversed, such that the generators are associated with the surgical instrument 12 and the receivers are positioned elsewhere. Although not limited thereto, the localizing device 22 may be affixed to an underneath side of the operating table that supports the patient.

In operation, the field generators generate magnetic fields which are detected by the sensor. By measuring the magnetic fields generated by each field generator at the sensor, the location and orientation of the sensor may be computed, thereby determining position data for the surgical instrument 12. Although not limited thereto, exemplary electro-magnetic tracking subsystems are further described in U.S. Pat. Nos. 5,913,820; 5,592,939; and 6,374,134 which are incorporated herein by reference. In addition, it is envisioned that other types of position tracking devices are also within the scope of the present teachings. For instance, non line-of-sight tracking subsystem 20 may be based on sonic emissions or radio frequency emissions. In another instance, a rigid surgical instrument, such as a rigid endoscope may be tracked using a line-of-sight optical-based tracking subsystem (i.e., LED's, passive markers, reflective markers, etc).

Position data such as location and/or orientation data from the tracking subsystem 20 is in turn relayed to the data processor 16. The data processor 16 is adapted to receive position/orientation data from the tracking subsystem 20 and operable to render a volumetric perspective image and/or a surface rendered image of the region of interest. The volumetric perspective and/or surface image is rendered 36 from the scan data 32 using rendering techniques well known in the art. The image data may be further manipulated 38 based on the position/orientation data for the surgical instrument 12 received from tracking subsystem 20. Specifically, the volumetric perspective or surface rendered image is rendered from a point of view which relates to position of the surgical instrument 12. For instance, at least one electro-magnetic sensor 24 may be positioned at the tip of the surgical instrument 12, such that the image is rendered from a leading point on the surgical instrument. In this way, the surgical instrument navigation system 10 according to various embodiments is able, for example, to visually simulate a virtual volumetric scene of an internal cavity from the point of view of the surgical instrument 12 residing in the cavity without the use of an endoscope. It is readily understood that tracking two or more electro-magnetic sensors 24 which are embedded in the surgical instrument 12 enables orientation of the surgical instrument 12 to be determined by the system 10.

As the surgical instrument 12 is moved by the surgeon within the region of interest, its position and orientation are tracked and reported on a real-time basis by the tracking subsystem 20. The volumetric perspective image may then be updated by manipulating 38 the rendered image data 36 based on the position of the surgical instrument 12. The manipulated volumetric perspective image is displayed 40 on a display device 18 associated with the data processor 16. The display 18 is preferably located such that it can be easily viewed by the surgeon during the medical procedure. In one embodiment, the display 18 may be further defined as a heads-up display or any other appropriate display. The image may also be stored by data processor 16 for later playback, should this be desired.

It is envisioned that the primary perspective image 38 of the region of interest may be supplemented by other secondary images. For instance, known image processing techniques may be employed to generate various multi-planar images of the region of interest. Alternatively, images may be generated from different view points as specified by a user 39, including views from outside of the vessel or cavity or views that enable the user to see through the walls of the vessel using different shading or opacity. In another instance, the location data of the surgical instrument may be saved and played back in a movie format. It is envisioned that these various secondary images may be displayed simultaneously with or in place of the primary perspective image.

In addition, the surgical instrument 12 may be used to generate real-time maps corresponding to an internal path traveled by the surgical instrument or an external boundary of an internal cavity. Real-time maps are generated by continuously recording the position of the instrument's localized tip and its full extent. A real-time map is generated by the outermost extent of the instrument's position and minimum extrapolated curvature as is known in the art. The map may be continuously updated as the instrument is moved within the patient, thereby creating a path or a volume representing the internal boundary of the cavity. It is envisioned that the map may be displayed in a wire frame form, as a shaded surface or other three-dimensional computer display modality independent from or superimposed on the volumetric perspective image 38 of the region of interest. It is further envisioned that the map may include data collected from a sensor embedded into the surgical instrument, such as pressure data, temperature data or electro-physiological data. In this case, the map may be color coded to represent the collected data.

Figure 3:
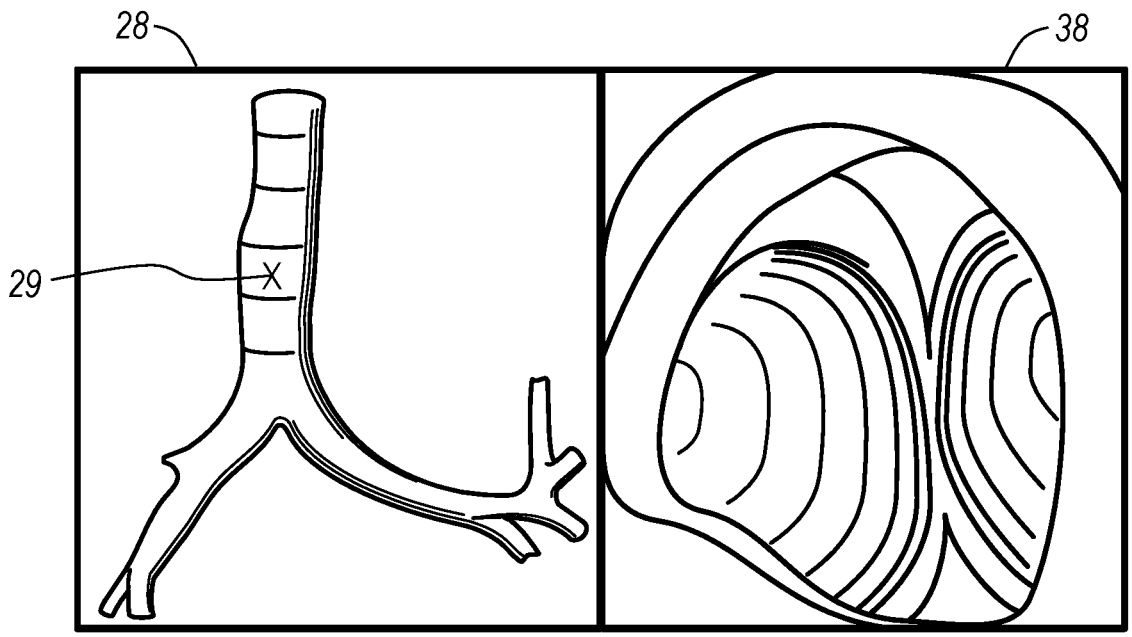
FIG. 3 is an exemplary display from the surgical instrument navigation system according to various embodiments.

FIG. 3 illustrates another type of secondary image 28 which may be displayed in conjunction with the primary perspective image 38. In this instance, the primary perspective image is an interior view of an air passage within the patient 13. The secondary image 28 is an exterior view of the air passage which includes an indicia or graphical representation 29 that corresponds to the location of the surgical instrument 12 within the air passage. In FIG. 3, the indicia 29 is shown as a crosshairs. It is envisioned that other indicia may be used to signify the location of the surgical instrument in the secondary image. As further described below, the secondary image 28 is constructed by superimposing the indicia 29 of the surgical instrument 12 onto the manipulated image data 38.

Figure 4:
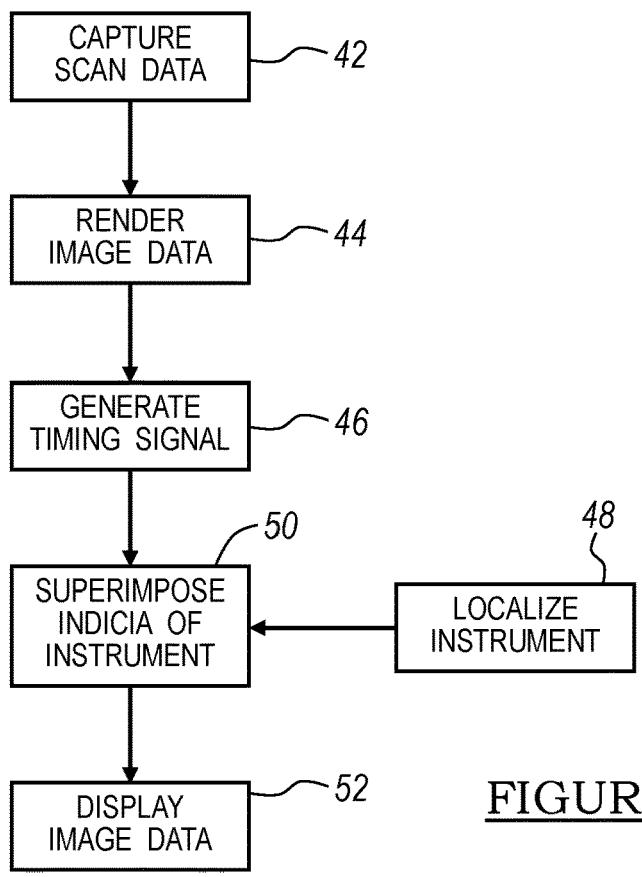
FIG. 4 is a flowchart that depicts a technique for synchronizing the display of an indicia or graphical representation of the surgical instrument with cardiac or respiratory cycle of the patient according to various embodiments.

Referring to FIG. 4, the display of an indicia of the surgical instrument 12 on the secondary image may be synchronized with an anatomical function, such as the cardiac or respiratory cycle, of the patient. In certain instances, the cardiac or respiratory cycle of the patient may cause the surgical instrument 12 to flutter or jitter within the patient. For instance, a surgical instrument 12 positioned in or near a chamber of the heart will move in relation to the patient's heart beat. In these instance, the indicia of the surgical instrument 12 will likewise flutter or jitter on the displayed image 40. It is envisioned that other anatomical functions which may effect the position of the surgical instrument 12 within the patient are also within the scope of the present teachings.

To eliminate the flutter of the indicia on the displayed image 40, position data for the surgical instrument 12 is acquired at a repetitive point within each cycle of either the cardiac cycle or the respiratory cycle of the patient. As described above, the imaging device 14 is used to capture volumetric scan data 42 representative of an internal region of interest within a given patient. A secondary image may then be rendered 44 from the volumetric scan data by the data processor 16.

In order to synchronize the acquisition of position data for the surgical instrument 12, the surgical instrument navigation system 10 may further include a timing signal generator 26. The timing signal generator 26 is operable to generate and transmit a timing signal 46 that correlates to at least one of (or both) the cardiac cycle or the respiratory cycle of the patient 13. For a patient having a consistent rhythmic cycle, the timing signal might be in the form of a periodic clock signal. Alternatively, the timing signal may be derived from an electrocardiogram signal from the patient 13. One skilled in the art will readily recognize other techniques for deriving a timing signal that correlate to at least one of the cardiac or respiratory cycle or other anatomical cycle of the patient.

As described above, the indicia of the surgical instrument 12 tracks the movement of the surgical instrument 12 as it is moved by the surgeon within the patient 13. Rather than display the indicia of the surgical instrument 12 on a real-time basis, the display of the indicia of the surgical instrument 12 is periodically updated 48 based on the timing signal from the timing signal generator 26. In one exemplary embodiment, the timing generator 26 is electrically connected to the tracking subsystem 20. The tracking subsystem 20 is in turn operable to report position data for the surgical instrument 12 in response to a timing signal received from the timing signal generator 26. The position of the indicia of the surgical instrument 12 is then updated 50 on the display of the image data. It is readily understood that other techniques for synchronizing the display of an indicia of the surgical instrument 12 based on the timing signal are within the scope of the present teachings, thereby eliminating any flutter or jitter which may appear on the displayed image 52. It is also envisioned that a path (or projected path) of the surgical instrument 12 may also be illustrated on the displayed image data 52.

Figure 5:
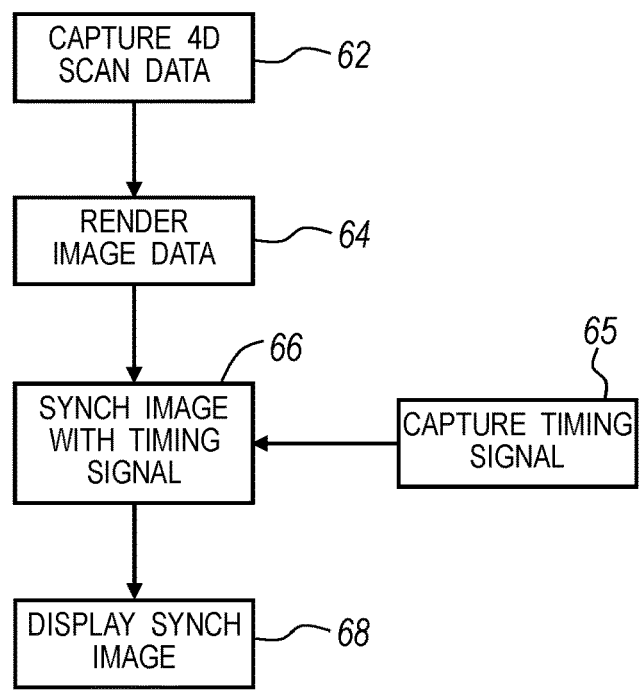
FIG. 5 is a flowchart that depicts a technique for generating four-dimensional image data that is synchronized with the patient according to various embodiments.

According to various embodiments the surgical instrument navigation system 10 may be further adapted to display four-dimensional image data for a region of interest as shown in FIG. 5. In this case, the imaging device 14 is operable to capture volumetric scan data 62 for an internal region of interest over a period of time, such that the region of interest includes motion that is caused by either the cardiac cycle or the respiratory cycle of the patient 13. A volumetric perspective view of the region may be rendered 64 from the volumetric scan data 62 by the data processor 16 as described above. The four-dimensional image data may be further supplemented with other patient data, such as temperature or blood pressure, using coloring coding techniques.

In order to synchronize the display of the volumetric perspective view in real-time with the cardiac or respiratory cycle of the patient, the data processor 16 is adapted to receive a timing signal from the timing signal generator 26. As described above, the timing signal generator 26 is operable to generate and transmit a timing signal that correlates to either the cardiac cycle or the respiratory cycle of the patient 13. In this way, the volumetric perspective image may be synchronized 66 with the cardiac or respiratory cycle of the patient 13. The synchronized image 66 is then displayed 68 on the display 18 of the system. The four-dimensional synchronized image may be either (or both of) the primary image rendered from the point of view of the surgical instrument or the secondary image depicting the indicia of the position of the surgical instrument 12 within the patient 13. It is readily understood that the synchronization process is also applicable to two-dimensional image data acquire over time.

To enhance visualization and refine accuracy of the displayed image data, the surgical navigation system can use prior knowledge such as the segmented vessel structure to compensate for error in the tracking subsystem or for inaccuracies caused by an anatomical shift occurring since acquisition of scan data. For instance, it is known that the surgical instrument 12 being localized is located within a given vessel and, therefore should be displayed within the vessel. Statistical methods can be used to determine the most likely location within the vessel with respect to the reported location and then compensate so the display accurately represents the instrument 12 within the center of the vessel. The center of the vessel can be found by segmenting the vessels from the three-dimensional datasets and using commonly known imaging techniques to define the centerline of the vessel tree. Statistical methods may also be used to determine if the surgical instrument 12 has potentially punctured the vessel. This can be done by determining the reported location is too far from the centerline or the trajectory of the path traveled is greater than a certain angle (worse case 90 degrees) with respect to the vessel. Reporting this type of trajectory (error) is very important to the clinicians. The tracking along the center of the vessel may also be further refined by correcting for motion of the respiratory or cardiac cycle, as described above.

The surgical instrument navigation system according to various embodiments may also incorporate atlas maps. It is envisioned that three-dimensional or four-dimensional atlas maps may be registered with patient specific scan data or generic anatomical models. Atlas maps may contain kinematic information (e.g., heart models) that can be synchronized with four-dimensional image data, thereby supplementing the real-time information. In addition, the kinematic information may be combined with localization information from several instruments to provide a complete four-dimensional model of organ motion. The atlas maps may also be used to localize bones or soft tissue which can assist in determining placement and location of implants.

While the teachings have been described according to various embodiments, it will be understood that the teachings are capable of modification without departing from the spirit of the teachings as set forth in the appended claims.

What is claimed is:

1. A navigation system to track a surgical instrument relative to a patient, comprising:
   an input configured to receive scan image data from an imaging device, wherein the scan image data corresponds to an external scan of a region of interest of the patient and includes encapsulated image data of an interior of the patient in the region of interest;
   a tracking subsystem operable to capture in real-time position data indicative of the position of the surgical instrument;
   a data processor adapted to receive the scan image data representative of the region of interest of a given patient and the position data from the tracking subsystem, the data processor being operable to render an image of the region of interest from a point of view which relates to the position of the surgical instrument, the image being derived from the scan image data; and
   a display in data communication with the data processor, the display being operable to display the image of the patient;
   wherein the surgical instrument is configured to move through the region of interest;
   wherein the data processor is operable to create a map of the area through which the surgical instrument is moved by determining the real time location and orientation of the surgical instrument over time based on the tracking subsystem capture of position data indicative of the surgical instrument over time;
   wherein the display is further operable to provide a virtual volumetric scan of an internal body of the patient from a point of view of the surgical instrument based upon the external scan of the region of interest.

2. The navigation system of claim 1, wherein the data processor is further operable to determine in real-time the location and orientation of the surgical instrument as the surgical instrument is moved within the region of interest and the display is further operable to display the location and orientation of the surgical instrument.

3. The navigation system of claim 1, wherein the map is a real-time map that is generated and corresponds to a path traveled by the surgical instrument through the region of interest.

4. The navigation system of claim 3, wherein the real-time map is generated by an outermost extent of the tracked position of the surgical instrument and a minimum extrapolated curvature of the surgical instrument.

5. The navigation system of claim 3, wherein the display is further operable to display the real-time map;
   wherein the real-time map and the image of the patient are displayed simultaneously.

6. The navigation system of claim 5, wherein the real-time map is displayed superimposed on the image of the patient.

7. The navigation system of claim 5, further comprising:
   a sensor embedded into the surgical instrument;
   wherein the sensor is configured to collect sensor date within the region of interest;
   wherein the real-time map is color coded to represent the collected sensor data.

8. The navigation system of claim 7, wherein the collected sensor data within the region of interest includes at least one of pressure data, temperature data, or electro-physiological data.

9. The navigation system of claim 1, further comprising a timing signal generator operable to generate a timing signal, wherein:
   the timing signal correlates to an anatomical function;
   the tracking subsystem is operable to (i) receive the timing signal from the timing signal generator, and (ii) in response to the timing signal and the position data, update the position of the surgical instrument to compensate for the anatomical function;
   the data processor is operable to superimpose indicia of the surgical instrument onto the rendered image based on the position; and
   the rendered image is a volumetric perspective image.

10. The navigation system of claim 9, wherein the anatomical function is a cardiac cycle or a respiratory cycle.

11. The navigation system of claim 10, wherein the data processor is configured to reduce flutter or jitter in the rendered image using the timing signal.

12. The navigation system of claim 9, wherein the data processor is operable to periodically update the superimposed indicia of the surgical instrument onto the rendered image based on the timing signal from the timing signal generator.

13. The navigation system of claim 1, wherein the map is a real-time map that corresponds to an external boundary of an internal cavity of the patient.

14. The navigation system of claim 1, wherein:
   the data processor is configured to compensate for an inaccuracy in a tracked first position of the surgical instrument caused by an anatomical shift of a first anatomical member of the patient having occurred subsequent to the acquisition of the scan data, the compensating for the inaccuracy including, determining a most likely position of the surgical instrument based on the tracked first position, determining whether the first position is greater than or equal to a predetermined distance away from the most likely position, and generating a trajectory error if the first position is greater than or equal to the predetermined distance away from the most likely position.

\* \* \* \* \*

UNITED STATES PATENT AND TRADEMARK OFFICE
CERTIFICATE OF CORRECTION

PATENT NO. : 11,426,254 B2
APPLICATION NO. : 16/725386
DATED : August 30, 2022
INVENTOR(S) : Laurent Verard et al.

It is certified that error appears in the above-identified patent and that said Letters Patent is hereby corrected as shown below:

On the Title Page

Column 1, Line 1, delete "(60)" and insert --(62)-- therefor

Non-Patent Literature Documents, in Other Publications, Page 2, Column 2, Line 9, delete "geodesci" and insert --geodesic-- therefor Signed and Sealed this
Twenty-second Day of November, 2022

Katherine Kelly Vidal
*Director of the United States Patent and Trademark Office*